United States Patent [19]

Nagano et al.

[11] Patent Number: 4,807,989
[45] Date of Patent: Feb. 28, 1989

[54] SURGICAL MICROSCOPE SYSTEM

[75] Inventors: Takashi Nagano, Hachioji; Toshiyuki Tsunoda, Sagamihara; Takashi Fukaya, Hachioji, all of Japan

[73] Assignee: Olympus Optical Co., Ltd., Japan

[21] Appl. No.: 1,585

[22] Filed: Jan. 9, 1987

[30] Foreign Application Priority Data

Jan. 14, 1986 [JP] Japan .................. 61-5259
Feb. 28, 1986 [JP] Japan .................. 61-41373

[51] Int. Cl.⁴ .............................................. A61B 3/10
[52] U.S. Cl. ..................... 351/212; 351/211; 351/206
[58] Field of Search ................ 351/212, 211, 221, 206

[56] References Cited

U.S. PATENT DOCUMENTS

| | | | |
|---|---|---|---|
| 4,046,463 | 9/1977 | La Russa et al. | 351/212 |
| 4,157,859 | 6/1979 | Terry | 351/212 |
| 4,375,320 | 3/1983 | Smirmaul | 351/212 |
| 4,410,242 | 10/1983 | Mueller et al. | 351/212 |
| 4,429,960 | 2/1984 | Mocilac et al. | 351/212 |
| 4,439,025 | 3/1984 | Smirmaul | 351/212 |
| 4,490,022 | 12/1984 | Reynolds | 351/212 |
| 4,660,947 | 4/1987 | Amolis | 351/212 |
| 4,666,269 | 5/1987 | Nakamura et al. | 351/212 |

FOREIGN PATENT DOCUMENTS 2614273 10/1977 Fed. Rep. of Germany.
3135703 5/1982 Fed. Rep. of Germany.

Primary Examiner—Rodney B. Bovernick
Assistant Examiner—P. M. Dzierzynski
Attorney, Agent, or Firm—Ostrolenk, Faber, Gerb & Soffen

[57] ABSTRACT

A surgical microscope comprises an illuminating light source for observation and/or photographing, an observation optical system, an index projecting optical system and a cornea configuration measuring optical system. The index projecting optical system includes an index which is removably inserted in the illuminating light beam emitted from the illuminating light source and transmitted through an objective of the observation optical system, thereby dispensing with any particular light source for measuring a cornea configuration, and a cornea configuration measuring mode and a photographing mode being automatically changeable by automatically detecting the presence or absence of the index within the optical path of the microscope.

16 Claims, 8 Drawing Sheets

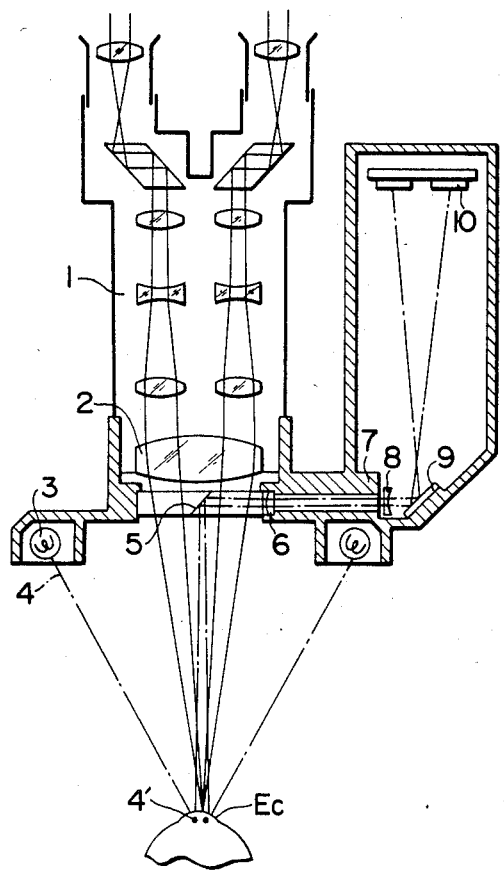
FIG. 1
(PRIOR ART)
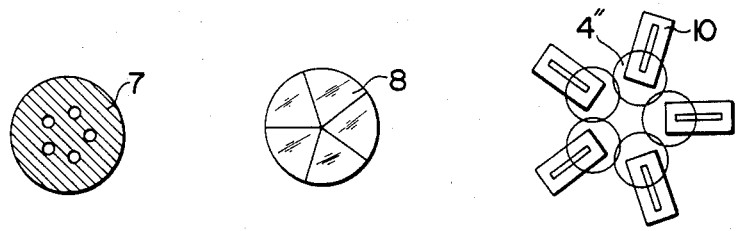
FIG. 2
(PRIOR ART)
FIG. 3
(PRIOR ART)
FIG. 4
(PRIOR ART)

SURGICAL MICROSCOPE SYSTEM

BACKGROUND OF THE INVENTION

The present invention relates to a surgical microscope system, and more particularly, to a surgical microscope system for performing a microscopic surgical operation.

In recent years, the so-called microsurgery of performing a microscopic surgical operation while observing with a microscope is widely used in public. The so-called microsurgery, which makes it possible to perform a high precision microscopic surgical operation, has greatly contributed to the wide fields including the ophthalmology, neurosurgery, otorhinolaryngology, plastic surgery and the like. Particularly, there has been an increasing demand in the field of ophthalmology for performing a cornea operation by measuring a radius of curvature of the cornea and controlling the extent of a suturing operation in accordance with the measured value so as to prevent the corneal astigmatism from occurring after the operation. To meet the demand, for example, Japanese Laid-Open Publication No. Sho 59/1984- 155232 discloses an apparatus for measuring the cornea configuration which is mounted on a surgical microscope in a unitary manner therewith. The apparatus will be described hereinafter with reference to FIGS. 1 to 4.

In FIG. 1, a surgical microscope includes a body 1, an objective lens 2, a light source 3 such as a circular fluorescent lamp for illuminating a projection index 4. When the index 4 is projected onto a cornea Ec of an eye to be measured, a reflected image 4' (virtual image) of the cornea Ec is formed to the index 4 by the convex-mirror action of the cornea Ec. The reflected image 4' varies in its size in accordance with a curvature of the radius of the cornea Ec. When the cornea Ec has regular astigmatism, the reflected image 4' is in an elliptic form and when the cornea Ec has irregular astigmatism, the reflected image 4' is in an irregular form. For this reason, it is possible to determine a surface configuration of the cornea Ec by measuring the reflected image 4' thereof.

An optical path change member 5 is provided in an optical system for measuring a cornea configuration which has a reflecting surface oblique to the exterior of an observation optical system in a space between the binocular observation optical paths. The optical path change member 5 is fixed adjacent to the objective lens 2 to the microscope body 1.

Reference numeral 6 is an objective lens of the cornea configuration measuring optical system. A diaphragm plate 7 is disposed adjacent to the rear side focus of the objective lens 6. A deflecting prism 8 is fixed adjacent to the rear side of the diaphragm plate 7. The diaphragm plate 7 has, for example, five small trough-holes at its center portion, as shown in FIG. 2. The deflecting prism 8 is in such a form as five prism pieces of the wedge type are put together in a unitary form, as shown in FIG. 3. The through-hole openings of the diaphragm plate 7 agree with the respective centers of the prism pieces of the deflecting prism 8. Projecting light beams from the reflected image 4' incident upon the objective lens 6 are divided into five beams through the openings of the diaphragm plate 7 and the deflecting prism 8. The five beams are then reflected by a reflecting mirror 9 to form images respectively upon light receiving surfaces of detector elements 10, such as one dimensional photo-diode array. The five detector elements 10 are arranged respectively at positions where projected images 4'' are formed to the reflected image 4', for example, as shown in FIG. 4.

With the cornea configuration measuring device of the structure just described above, a measuring switch (not shown) is turned on and at the same time a configuration of the reflected image 4' is detected by the detector elements 10. The detected signals are electrically amplified and calculated by a signal operating circuit (not shown) to determine the major and minor axes of an ellipse and the elliptic axes for the reflected image 4'. From these data a radius of curvature, a degree of astigmatism, an axial angle of astigmatism and the like are determined and displayed. When the cornea reflected image is not circular or elliptic because of irregular astigmatism, radii of curvature are determined and displayed respectively for meridional directions of the cornea.

Since a conventional apparatus is constructed as described above, it is necessary to provide a light source only for the cornea configuration measurement in addition to an illumination light source for observation or photographing. In addition, switches are provided for respective light sources. As a result, the apparatus becomes bulky, expensive and complicated in operation. Furthermore, since it is very troublesome to remove the measuring device from the apparatus after the cornea configuration measurement is completed, an operation must be performed with the measuring device attached to the apparatus between the objective lens and eyes to be measured, resulting in difficulty in operation, that is very dangerous.

SUMMARY OF THE INVENTION

It is an object of the present invention to provide a surgical microscope which is capable of measuring a cornea configuration with a simple and inexpensive structure and an easy and safe operation.

According to the present invention, the surgical microscope comprises an illumination light source for observation and/or photographing, an observation optical system, an index projecting optical system and a cornea configuration measuring optical system, the index projecting optical system including an index which is removably inserted in illumination light beams emitted from the illumination light source and passing through an objective lens of the observation optical system, thereby dispensing with a particular light source and its switch for measuring the cornea configuration and securing an operation space with a simple operation except during the measurement.

Besides, according to the present invention, a perforated index which is illuminated by a light source for photographing of the surgery microscope is insertably disposed in the microscope optical path between the objective lens and an eye to be measured and a detector is provided for detecting whether the perforated index lies with the microscope optical path, whereby a cornea configuration measuring mode and a photographing mode are automatically switched with an output from the detector when the perforated index lies within the microscope optical path or not, respectively, thus allowing an operator to concentrate his attention on an operation.

Furthermore, according to the present invention, since the cornea configuration can be measured with a light source for photographing and its switching operation, any particular light source and its switch for measuring the cornea configuration can be dispensed with, so that it is possible to provide an inexpensive surgery microscope which is improved in operation and has a compact and simple structure. In addition, since an illumination during the cornea configuration measurement is given by a bright light source for an electronic flashlight emission, it is possible to momentarily perform the measurement even with a photosensitive element of low sensitivity. The cornea configuration measuring and the photographing modes can be automatically switched by detecting whether the index exists or not and in order to develop a trigger signal only a single switch, for example, may be arranged at a proximal portion, so that it is still possible to easily operate and to allow an operator to concentrate his attention on the operation. Upon completion of the cornea configuration measurement, it is possible to simply remove the index so as to make a surgical operation safe and reliable.

BRIEF DESCRIPTION OF THE DRAWINGS

FIG. 1 is a schematic diagram illustrating an example of an optical system of a conventional surgical microscope;

FIGS. 2 to 4 are diagrams viewing a diaphragm plate, a deflecting prism and a detector element from the direction of the optical axis in the example shown in FIG. 1, respectively;

DESCRIPTION OF THE PREFERRED EMBODIMENTS

Figure 5:
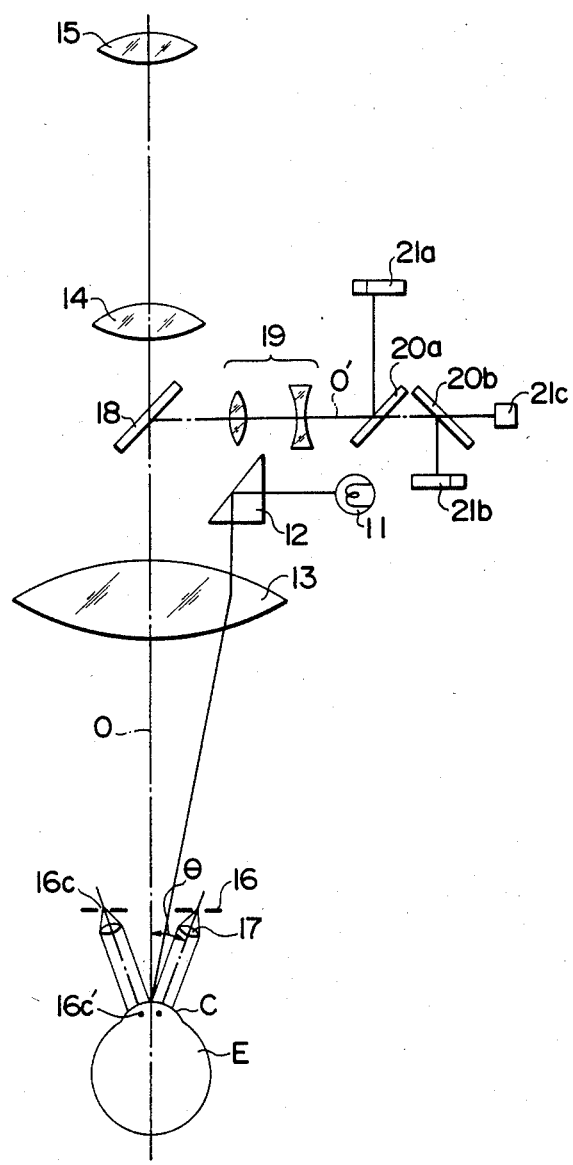
FIG. 5 is a schematic diagram illustrating an optical system of a first embodiment of surgical microscopes according to the present invention.

In FIG. 5, which illustrates an optical system of a first embodiment of the present invention, E designates an eye to be measured and C designates a cornea of the eye E. An illumination light source 11 such as a halogen lamp illuminates the eye E through an objective lens 13 by light beams reflected by a prism 12 and thus forms the so-called coaxial illumination optical system of a surgical microscope. The objective lens 13, a relay lens 14 and an eyepiece 15 form an observation optical system of the surgical microscope. Although not shown, pairs of the relay lens 14 and the eyepiece 15 are disposed in symmetry with respect to the optical axis O of the objective lens 13 in a plane perpendicular to the drawing sheet so as to stereoscopically observe the eye E with right and left eyes of an observer.

Figure 6:
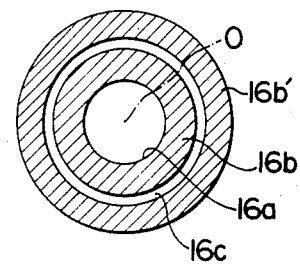
FIG. 6 is a diagram viewing a perforated slit plate of the first embodiment shown in FIG. 5 from the direction of the optical axis.
Figure 7:
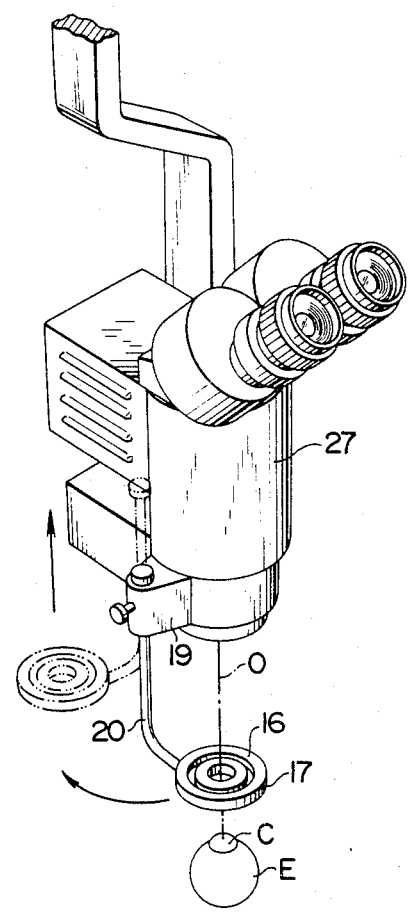
FIG. 7 is a perspective view illustrating a structure attaching the perforated slit plate and a collimator lens.

Next, an index projecting optical system will be described. Light beams emitted from the light source 11 pass through the prism 12 and the objective lens 13 to illuminate an index provided by perforated slit plate 16. The slit plate 16 has a central opening 16a, as shown in FIG. 6, viewed from the direction of the optical axis of the surgical microscope and further includes shade plates 16b, 16b' around the periphery of the hole 16a. An annular belt-shaped slit 16c is provided between the shade plates 16b, 16b'. Light beams passing through the slit 16c impinge upon the cornea C of the eye E after passed through a collimator lens 17. The collimator lens 17 forms a cylindrical lens which has the refractive power in each of meridian surfaces and has no refractive power in a surface perpendicular to each of the meridian surface, that is, a surface including a ring-shaped circumference. The collimator lens 17 is disposed at a distance of its focal length from the slit 16c, which makes light rays appeared from the slit 16c parallel so as to project the light rays from the optically infinite point onto the cornea C. Light rays appeared from the slit 16c have the same angle $\theta$ around the optical axis O. A virtual image 16' of the annular slit 16c is formed on the cornea C by mirror reflection. The slit plate 16 and the collimator lens 17 are attached to a microscope body 27, as shown in FIG. 7, which are integrally supported by a slide arm 20 fixed into a guide 19 provided on the microscope body 27. The slide arm 20 is insertable at a predetermined position in such a manner that it is rotatable around an axis parallel to the optical axis of the microscope and is movable up and down in the direction of the optical axis.

Figure 8:
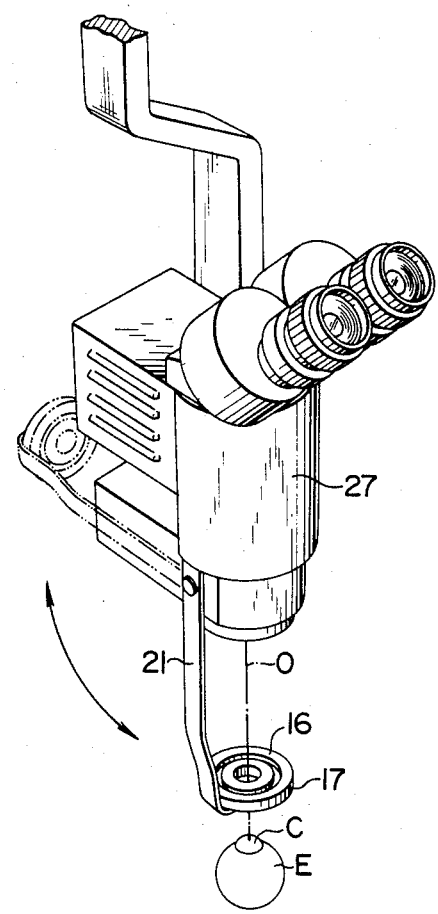
FIGS. 8 and 9 are perspective views illustrating modifications of the structure shown in FIG. 7, respectively.
Figure 9:
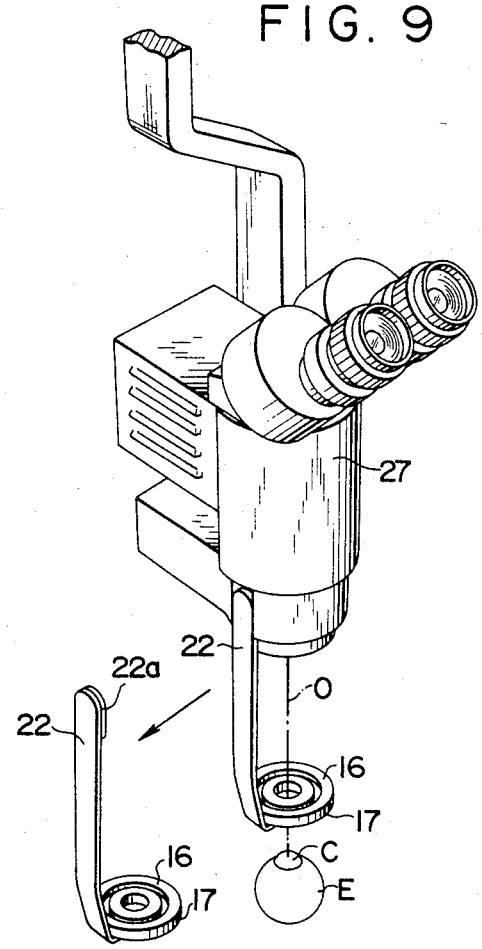

FIGS. 8 and 9 show modifications of a structure including the perforated slit plate 16 and the collimator lens 17. The slit plate 16 and the collimator lens 17 are supported by a rotary arm 21 and a magnet arm or support member 22 to secure to the microscope body 27. In FIG. 8, the slit plate 16 and the collimator lens 17 are insertable in a predetermined position on the optical axis O of the microscope by turning the support member or arm 21. In FIG. 9, the slit plate 16 and the collimator lens 17 are insertable in a predetermined position on the optical axis O of the microscope by attaching the support member 22 to the microscope body 27 utilizing the magnetic force of a magnet portion 22a of the support member 22, resulting in a simple operation.

Figure 10:
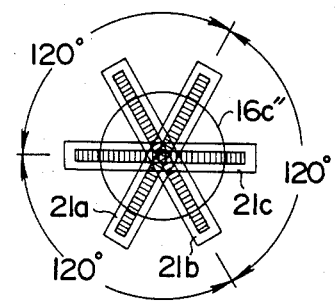
FIG. 10 is a diagram illustrating an arrangement of one-dimensional sensors viewed from the direction of the optical axis of the first embodiment shown in FIG. 5.

The cornea configuration measuring optical system will now be described hereinafter. The virtual image 16c' of the slit 16c which is formed on the cornea C of the eye E is transmitted through the collimator lens 17, the central opening 16a of the slit plate 16, the objective lens 13 and an interference filter 18 such as a dichroic mirror which transmits visible rays and reflects infrared rays. Accordingly, reflected infrared rays pass through a relay lens system 19 and further are transmitted through or reflected by half mirrors 20a, 20b and finally are formed in an image on three pieces of one-dimensional sensors 21a, 21b, such as CCDs which are sensitive to infrared rays. The sensors 21a, 21b, 21c as viewed from the direction of the optical axis O' are arranged, as shown in FIG. 10, so as to be angularly displaced with respect to each other by 120°.

Since the cornea C is generally regarded as a toric plane, even though the annular slit 16c is in a true circle, the virtual image 16c' on the cornea C and images 16c'' on the sensors 21a, 21b, 21c take a form of ellipse. Consequently, a radius of curvature r, a degree of astigmatism and an astigmatic axial angle A of the cornea C can be determined by measuring the elliptic configuration.

In general, the equation of an ellipse is expressed with reference to any coordinate axes X and Y as follows:

$$ax^2 + by^2 + 2cxy + dx + ey + 1 = 0$$

where a to e are five unknown quantities, which can be determined by taking coordinates of five points out of six on the image 16 formed on the three one-dimensional sensors 21a, 21b, 21c.

In operation, when the cornea configuration is measured, the optical axis of the eye E to be measured is aligned with the optical axis O of the microscope and a distance between the objective lens 13 and the cornea C of the eye E is adjusted by effecting a focusing operation with the microscope body 27 moving vertically together with the objective lens 13. Then, the cornea configuration is measured by interposing the slit plate 16 and the collimator lens 17 of the index projecting optical system at a predetermined position on the optical axis O between the objective lens 13 and the cornea C. In general, a binocular stereoscopic microscope has a large depth of focus and it is difficult to adjust a distance between the objective lens 13 and the cornea C of the eye E. Accordingly, while there may be some variations in the distance between the cornea C and the slit plate 16 and the collimator lens 17, such variations do not practically affect a measuring accuracy since an image of the slit 16c is projected onto the cornea C with parallel light rays.

Upon completion of the cornea configuration measurement, the slit plate 16 and the collimator lens 17 are immediately removed from the optical axis O so as not to interrupt a surgical operation to secure an operational space, resulting in a smooth and safe surgical operation.

In addition, as described above, no particular light source for measuring the cornea configuration is required, so that the apparatus is simple in structure and inexpensive.

Figure 11:
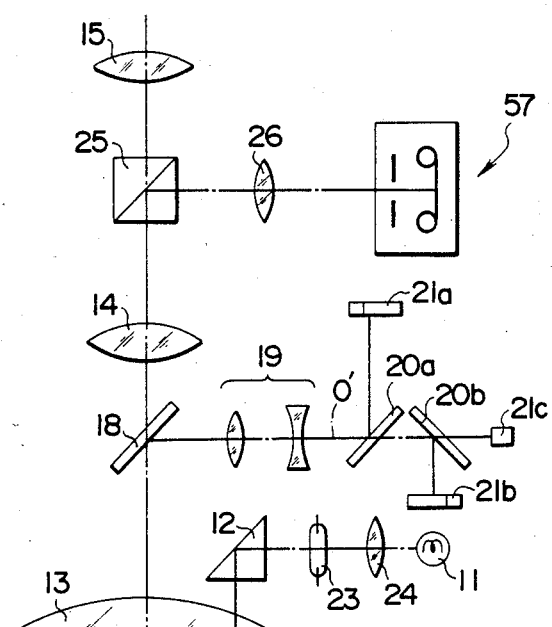
FIG. 11 is a schematic diagram illustrating an optical system of a second embodiment of surgical microscopes according to the present invention.
Figure 12:
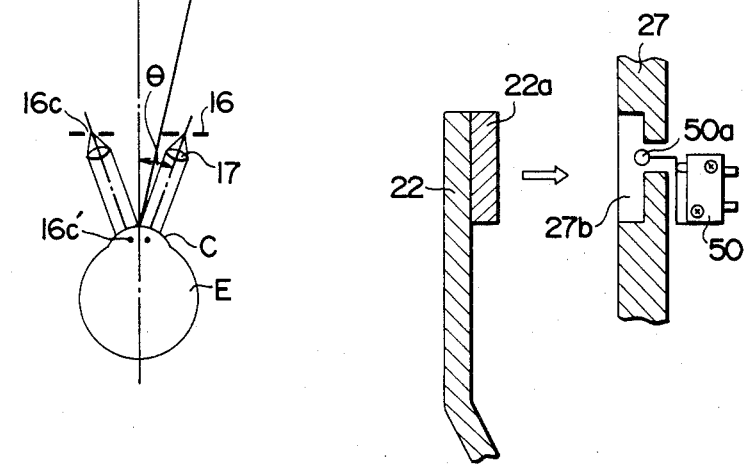
FIG. 12 is a partially sectional view illustrating an arrangement of an index detector and fixing a support member to a microscope body in the structure shown in FIG. 9.

FIG. 11 shows an optical system of a second embodiment of a surgical microscope according to the present invention. Like reference numerals designate like or corresponding parts and hence their descriptions will be omited.

In FIG. 11, the illumination light source 11 for observation, relay lens 24, flashlight emission source 23 for photographing, prism 12 and objective lens 13 constitute the so-called coaxial illumination optical system of the surgical microscope. The objective lens 13, relay lens 14 and eyepiece 15 constitute the observation optical system. The light source 11, prism 12, objective lens 13, perforated slit plate 16 and collimator lens 17 constitute the index projecting optical system. The flashlight emission source 23, prism 12, objective lens 13, perforated slit plate 16, collimator lens 17, dichroic mirror 18, relay lens system 19, half mirrors 20a, 20b and one-dimensional sensors 21a, 21b, 21c constitute the cornea configuration measuring optical system. The flashlight emission source 23, prism 12, objective lens 13, dichroic mirror 18, relay lens 14, beam splitter 25, image forming lens 26 and camera 57 constitute the photographing optical system.

Although not shown, the eyepieces 15 constitute a pair of optical system together with the relay lenses 14 in symmetry with respect to the optical axis O of the objective lens 13 on the plane perpendicular to the drawing sheet.

Both perforated slit plate 16 and the collimator lens 17 is removably attached to the microscope body 27 by means of the support member 22, as shown in FIG. 9. The magnet portion 22a of the magnet arm is insertable in the recess 27b formed in the side wall of the microscope body 27. The tip end of a movable contact piece 50a of a microswitch 50 is sticking out of the recess 27b, which is used as an index detector provided in the side wall of the microscope body 27 which will be described later.

Figure 13:
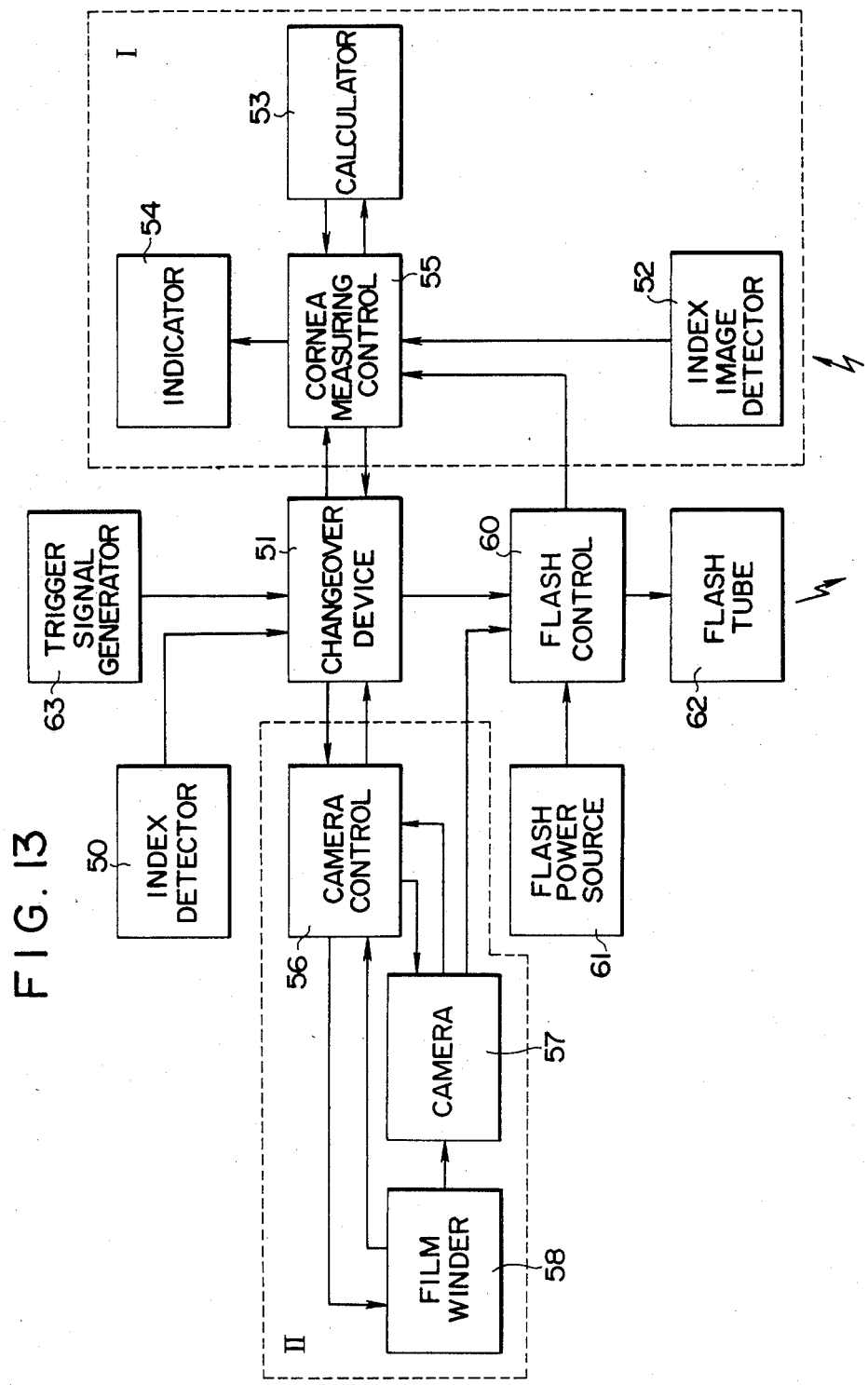
FIG. 13 is a block diagram of a circuit for automatically selecting a photographing and a cornea configuration measuring mode.

In FIG. 13, reference numerals 50 designates the above-mentioned index detector. A changeover device 51 includes a main switch (not shown) for turning a flashlight emission control on and off by selecting either of a cornea measuring control 55 and a camera control 56 which will be described later, in response to an output from the index detector 50. A portion I enclosed by a dotted lines forms the cornea configuration measuring system which includes an index image detector 52 for detecting an index image by cornea reflection, a calculator 53 for calculating parameters of a cornea configuration, a cornea measuring indicator 54 and the above-mentioned cornea measuring control 55 for controlling the index image detector 52, calculator 53 and cornea measuring indicator 54. A portion II enclosed by other dotted lines forms the photographing system which includes a camera 57, a film winder 58 and the above-mentioned camera control 56 for controlling the camera 57 and the winder 58 which are constituted so as to deliver a signal for indicating shutter opening conditions. In addition, there are provided a flashlight emission control 60 for controlling a flashlight power source 61 and a flashlight emission tube 62 and a trigger signal generating means 63 such as a foot switch and the like.

In operation, when the eye E to be inspected is observed, light rays from the illumination light source 11 for observation is reflected by the prism 24 to illuminate the eye E through the objective lens 13. At this time, it is possible to stereoscopically observe the eye E by observing a pair of the observation optical systems with the left and right eyes, which systems are constructed perpendicularly to the drawing sheet.

When a cornea configuration is measured, the support member 22 is first mounted at a predetermined position of the microscope body 27. The cornea configuration is measured by light rays from the flashlight emission source 23 in the same manner as described in the first embodiment. At this time, when the perforated slit plate 16 and the collimator lens 17 are inserted in the optical path by mounting the support member 22 on the microscope body 27, the contact piece 50a of the index detector 50 is pushed by the magnet portion 22a to produce a detection signal which is fed to the changeover device 51. The changeover device 51 selects one of the cornea configuration measuring control 55 and the camera control 56 in response to the signal from the image detector 50 and maintains the selected control on standby. On the other hand, a main switch (not shown) within the device also turns on to maintain the flashlight emission control 60 on standby. Consequently, the condition that a series of operations will be commenced by a trigger signal input from a trigger signal generating means 63 is caused. Consequently, assuming that the cornea configuration measuring control 55 is selected in the changeover device 51 by an output from the index detector 50 to be in the cornea configuration measuring mode, when a trigger signal is given from the trigger signal generating means 63 to the changeover device 51, it delivers the trigger signal to both the cornea configuration measuring control 55 and the flashlight emission control 60. Then, the cornea configuration measuring device 55 is ready for receiving an output from the index image detector 52. At the same time, the flashlight emission control 60 causes the flashlight emission tube 62 to emit flashlight by receiving the trigger signal. Also, a light amount detector (not shown) within the flashlight emission control 60 commences the photometric operation simultaneously with the commencement of flashlight emission. When a sufficient amount of light is reached, the emission control 60 causes the tube 62 terminate the flashlight emission and delivers a flashlight emission terminate signal to the cornea configuration measuring control 55. With the flashlight emission the index image detector 52 delivers an output corresponding to a configuration of an index image which is obtained by reflection of the cornea C of the eye E to the cornea configuration measuring control 55. When received the index image configuration output, the control 55 temporarily retains the output signal and inhibits an input from the index image detector 52 until the flashlight emission terminate signal from the emission control 60 is inputted to feed the retained data of the index image to the calculator 53. Then, the calculator 3 calculates parameters of the cornea configuration using the quadratic equation described above to feed an output through the control 55 to the cornea configuration measuring indicator 54 which displays the calculated results. At this time, it is to be understood that when the control 55 is directly connected to an exterior apparatus such as a personal computer or the like, the calculator 53 is not required. Thus, the cornea configuration can be measured by a series of operations described above.

In the photographing operation, the support member 22 is removed from the microscope body 27 to eliminate both the slit plate 16 and the collimator lens 17 from the optical path. When the eye E and the cornea C are illuminated through the prism 12 and the objective lens 13 by allowing the flashlight emission source 23 to emit flashlight, light rays from the cornea C is transmitted through the objective lens 13 to the dichroic mirror 18 in which only visible rays are transmitted. Part of the transmitted rays are reflected by the beam splitter 25 to take a photograph of the cornea C by the camera 57 through the image forming lens 26.

While the photographing mode is on with the series of operations described above after the support member 22 from the microscope body 27 is removed, the camera control 56 detects whether the film winding operation of the camera 57 is completed. When not completed, the camera control 56 causes the film winder 58 to operate. After the completion of the film winding, when the changeover device 51 receives a trigger signal from the trigger signal generating means 63, the device 51 transmits the trigger signal to the camera control 56. Then, the camera control 56 causes the camera 57 to release a shutter. When the shutter is fully opened, the camera 57 delivers a flashlight emission initiate signal to the flashlight emission control 60. Then, a flashlight emission and a photometric operation are performed in the same manner as in the cornea configuration measurement. When the shutter is closed, the camera control 56 receives photographing completion signal from the camera 57 to operate the film winder, whereby a film is wound. Thus, the photographing is performed by the above-mentioned series of operations.

As is clear from the foregoing, the support member 22 for supporting the slit plate 16 and the collimator lens 17 is easily and promptly detachable to the microscope body 27 except during the cornea configuration measurement, so as not to be hindrance to a surgical operation. With the microscope of the present invention, the cornea configuration measuring mode and the photographing mode are automatically switched depending upon whether the support member 22 is in the optical axis in response to an output from the index detector 50. Furthermore, since the recess 27b of the microscope body 27 in which the support member 22 is inserted is positioned at a predetermined distance, a relative distance between the slit plate 16 and the collimator lens 17 and the eye E under inspection is determined by a working distance of the objective lens when the microscope is brought into focus on the cornea while viewing through the microscope.

Although in the above embodiment the changeover device 51, the cornea configuration measuring control 55, the calculator 53 and the camera control 56 are separately provided, it will be easily understood that the controlling and the calculating operations may be achieved using a computer with software of the same functional structure. While the index detector 50 is constituted by a microswitch, it is further understood that the detector 50 is not limited thereto but may be a photo-interrupter or the like which is disposed so as to be interrupted by the support member 22 when the slit plate 16 and the collimator lens 17 are within the optical path.

As described above, according to the present invention, since the cornea configuration can be measured with the light source for photographing and its switch operation, no particular light source for cornea configuration measurement and its switch is required, so that it is possible to provide a compact and inexpensive surgical microscope of a simple structure and of an easy handling. In addition, since the illumination during the cornea configuration measurement is performed with a bright flashlight emission source, it is possible to use even a photosensitive element of low sensitivity and to effect the measurement momentarily. Furthermore, it is possible to effect either the cornea configuration measurement or the photographing by automatically detecting the presence of the index and to provide only one switch, for example, near the proximal portion of the microscope as the trigger signal generating means. Consequently, operations are not cumbersome and an operator can concentrate his attention on a surgical operation. Also, upon completion of the cornea configuration measurement the index can be easily removed, so that the ease and safety of operation are improved.

Figure 14:
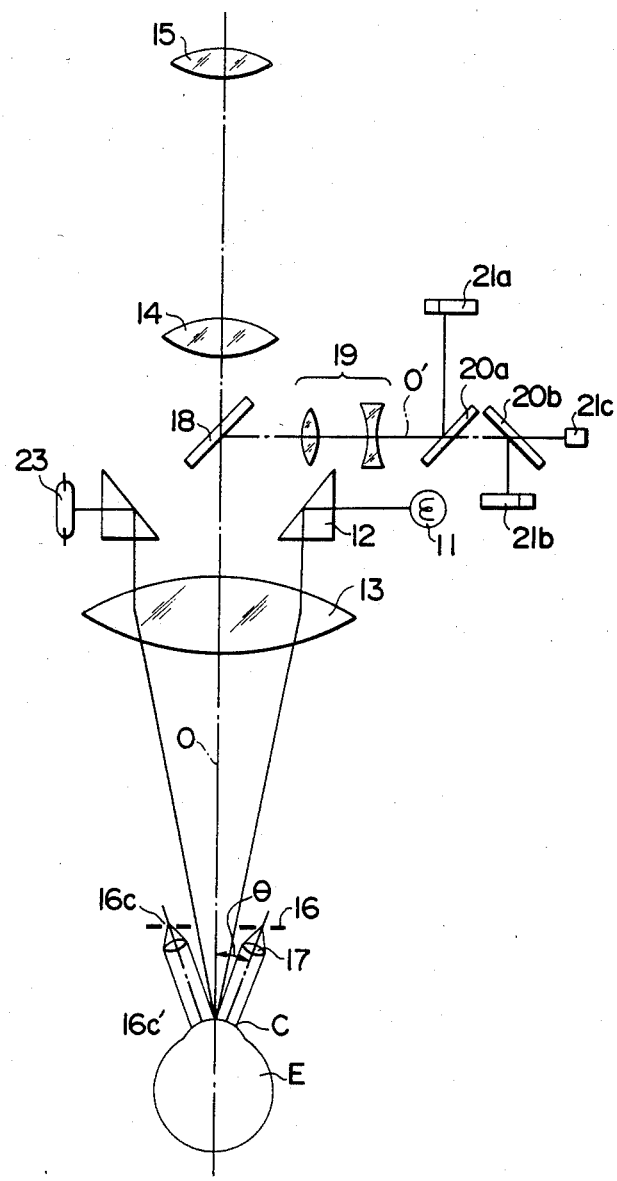
FIG. 14 is a schematic diagram illustrating an optical system of a third embodiment of surgical microscopes according to the present invention.

FIG. 14 shows another optical system utilizing a flashlight source for photographing which is housed within a surgical microscope as an illumination light source for the cornea configuration measurement according to a third embodiment of the present invention. The system causes the flashlight source 23 to emit light rays in synchronism with the time of the measurement

What is claimed is:

1. A surgical microscope system comprising:
   an illumination light source for observation;
   an observation optical system including an objective and an eyepiece;
   an index projecting optical system including an index which is removably inserted in an illumination light beam emitted from said illumination light source and transmitted through the objective of said observation optical system;
   said index including a slit plate disposed apart from the objective and removably mounted in said observation optical system to project a pattern of said slit plate on a cornea;
   a cornea configuration measuring optical system for measuring a cornea configuration by receiving light beams reflected by said index projecting optical system.

2. A surgical microscope system according to claim 1, in which said slit plate of said index projecting optical system is attached to a support arm member which is shiftably mounted on the microscope body to locate said slit plate on and off the predetermined position on the optical axis of the microscope.

3. A surgical microscope system according to claim 2, in which said support arm member is pivotally mounted on the microscope body to occupy a predetermined position apart from said objective and on the optical axis of the microscope.

4. A surgical microscope system according to claim 1, in which the slit plate when in said observation optical system is disposed between said objective and a cornea being observed by using said surgical microscope system.

5. A surgical microscope system according to claim 1, in which said index of said index projecting optical system comprises a perforated slit plate, said slit plate being formed of a shield plate with its center opening having an annular belt-shaped slit on the periphery of the opening.

6. A surgical microscope system according to claim 5, in which said opening of said slit plate allows an image of said annular belt-shaped slit reflected by the cornea of an eye to be measured to pass therethrough when measuring a cornea configuration.

7. A surgical microscope system comprising:
   an illumination light source for observation;
   an observation optical system including an objective and an eyepiece;
   an index projecting optical system including an index which is removably mounted in an illuminating light beam emitted from said illumination light source and transmitted through the objective of said observation optical system;
   a cornea configuration measuring optical system for measuring a cornea configuration by receiving light beams reflected by said index projecting optical system;
   said cornea configuration measuring optical system comprising an interference filter, a pair of half mirrors and photoelectric transducer elements which receive light beams reflected by and passing through said pair of half mirrors.

8. A surgical microscope system according to claim 7, in which said interference filter comprises a dichroic mirror which transmits visible rays and reflects infrared rays.

9. A surgical microscope system according to claim 9, in which said photoelectric transducer elements comprises three one-dimensional sensors which are sensitive to infrared rays and are angularly displaced with respect to each other by 120°.

10. A surgical microscope system comprising:
    an illumination light source for observation;
    an observation optical system including an objective and an eyepiece;
    an index projecting optical system including an index which is removably inserted in an illuminating light path of said observation optical system;
    a cornea configuration measuring optical system for measuring a cornea configuration by receiving an image reflected by the cornea of an eye to be measured in said index projecting optical system;
    a photographing optical system including a flashlight emission source for photographing and a camera; and
    an index detector for detecting whether said index has been inserted in the optical path of said observation optical system.

11. A surgical microscope system according to claim 10, in which said index detector automatically switches the photographing mode and the cornea configuration measuring mode in response to an output therefrom.

12. A surgical microscope system according to claim 10, in which said flashlight emission source of said photographing optical system is shared between said cornea configuration measuring optical system and said photographing optical system in an illumination light source, which emission source synchronously emits a flashlight when measuring the cornea configuration.

13. A surgical microscope system according to claim 10, in which said index detector comprises a microswitch.

14. A surgical microscope system according to claim 10, in which said illumination light source for observation is disposed in a conjugate relationship with said flashlight emission source for photographing with respect to a relay lens of said observation optical system.

15. A surgical microscope system comprising:
    an illumination light source for observation;
    an observation optical system including an objective and an eyepiece;
    an index projecting optical system including an index which is removably mounted in an illuminating light beam emitted from said illumination light source and transmitted through the objective of said observation optical system;
    a cornea configuration measuring optical system for measuring a cornea configuration by receiving light beams reflected by said index projecting optical system;
    said index of said index projecting optical system being attached to a support member which is removably mounted on the microscope body at a predetermined position on the optical axis of the microscope;
    said support member being attached to a guide member provided on the microscope body in such a manner that said support member is rotatable around an axis parallel to the optical axis of the microscope and vertically slidable in the direction of the optical axis.

16. A surgical microscope system comprising:

an illumination light source for observation;

an observation optical system including an objective and an eyepiece;

an index projecting optical system including an index which is removably mounted in an illuminating light beam emitted from said illumination light source and transmitted through the objective of said observation optical system;

a cornea configuration measuring optical system for measuring a cornea configuration by receiving light beams reflected by said index projecting optical system;

said index of said index projecting optical system being attached to a support member which is removably mounted on the microscope body at a predetermined position on the optical axis of the microscope;

said support member being provided with a magnet portion so as to be removably attached to the microscope at a predetermined position thereof.

* * * * *